(12) United States Patent
Gruenbeck et al.

(10) Patent No.: US 7,034,119 B2
(45) Date of Patent: Apr. 25, 2006

(54) METHOD FOR RECOMBINANT PRODUCTION OF POLYPEPTIDES

(75) Inventors: Rainer Gruenbeck, Penzberg (DE); Erhard Kopetzki, Penzberg (DE); Friedrich Popp, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 74 days.

(21) Appl. No.: 10/866,567

(22) Filed: Jun. 12, 2004

(65) Prior Publication Data

US 2005/0003485 A1    Jan. 6, 2005

(30) Foreign Application Priority Data

Jun. 12, 2003    (EP) .................................. 03012295

(51) Int. Cl.
*C07K 1/00*    (2006.01)

(52) U.S. Cl. ...................... 530/351; 530/412; 435/69.1; 436/6

(58) Field of Classification Search ................ 530/351, 530/412; 435/69.7; 436/6
See application file for complete search history.

(56) References Cited

OTHER PUBLICATIONS

Chrunyk et al., "Inclusion Body Formation and Protein Stability in Sequence Variants of Interleukin-1B," Journal of Biological Chemistry, (Aug. 25, 1993) 268(24) 18053-61.*
TAng et al., "Production of Human Proinsulin in *E.coli* in Non-Fusion Form," Biotechnology Letters, (Jul. 1993) 15 (7) 661-666.*
Chen et al., "Production of Human Insulin in an *E.coli* System with Met-Lys-Human Proinsulin as the Expressed Precursor," Applied Biochemistry and Biotechnology, (1995) 55(1) 5-15.*
Boye et al., "The Role of dam Methyltransferase in the Control of DNA Replication in *E.coli*," Cell, (1990) 62 (5): p. 981-989.*

* cited by examiner

*Primary Examiner*—Robert A. Wax
*Assistant Examiner*—Agnes Rooke
(74) *Attorney, Agent, or Firm*—George W. Johnston; Dennis P. Tramaloni

(57) ABSTRACT

A method for the recombinant production of a polypeptide by expressing a nucleic acid encoding said polypeptide in a microbial host cell, forming in the cytoplasm of said host cell inclusion bodies containing said polypeptide, and isolating, solubilizing and naturing said polypeptide, characterized in that after fermentation the host cell or the host cell content is incubated at a temperature of 40° C. or higher for at least 10 minutes and subsequently insoluble polypeptide is isolated from the host cell, this method providing an improved yield in inclusion bodies containing the desired polypeptide.

2 Claims, No Drawings

SEQUENCE LISTING

```
<160> NUMBER OF SEQ ID NOS: 4

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence:carrier
      peptide

<400> SEQUENCE: 1

Met Cys Asp Leu Pro Gln Thr His Ser Leu Gly Ser Arg
 1               5                  10

<210> SEQ ID NO 2
<211> LENGTH: 39
<212> TYPE: PRT
<213> ORGANISM: Artificial Sequence
<220> FEATURE:
<223> OTHER INFORMATION: Description of Artificial Sequence:target
      peptide

<400> SEQUENCE: 2

Trp Gln Glu Trp Glu Gln Lys Ile Thr Ala Leu Leu Glu Gln Ala Gln
 1               5                  10                  15

Ile Gln Gln Glu Lys Asn Glu Tyr Glu Leu Gln Lys Leu Asp Lys Trp
                20                  25                  30

Ala Ser Leu Trp Glu Trp Phe
            35

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence:primer N1
```

-continued

```
<400> SEQUENCE: 3
aaaaaagcgg ccgcgacaat tcgcgcgcga aggcg                    35

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence:primer N2

<400> SEQUENCE: 4
aaaaaagcgg ccgctcactg cccgctttcc agtcgg                  36
```

METHOD FOR RECOMBINANT PRODUCTION OF POLYPEPTIDES

FIELD OF THE INVENTION

The invention relates to an improved method for the recombinant production of polypeptides in prokaryotes via inclusion bodies.

BACKGROUND OF THE INVENTION

In prokaryotic organisms, the protein synthesis, also referred to as translation, takes place on the ribosomes in the cytoplasm. In expressing recombinant DNA in prokaryotic host organisms, such as, e.g., *E. coli*, it is often desirable that the resultant recombinant gene product/protein should be precipitated in the cytoplasm in the form of insoluble "inclusion bodies". After completion of fermentation and lysis of the cells, the inclusion bodies are isolated and optionally purified and the recombinant protein contained therein is solubilized by adding denaturants such as urea or guanidinium hydrochloride and maturation of said protein is accomplished by reducing the denaturing conditions. Such methods are well-known and have long been used successfully also for the industrial manufacture of recombinant proteins (cf., e.g., Lee, S. Y., Trends Biotechnol. 14 (1996) 98–105; Panda, A. K., et al., J. Biotechnol. 75 (1999) 161–172; Mattes, R., Semin. Thromb. Hemost. 27 (2001) 325–336; Clark, E. D., Curr. Opin. Biotechnol. 12 (2001) 202–207; Misawa, S., and Kumagai, I., Biopolymers 51 (1999) 297–307; and Lilie, H., Current Opinion Biotechnol. 9 (1998) 497–501).

The extent to which the proteins expressed in the cytoplasm are obtained as insoluble protein aggregates (inclusion bodies) or in soluble active or inactive form is determined essentially by the primary structure (amino acid sequence) of the protein. The primary structure of the protein determines the intrinsic biophysical/biochemical properties of the protein, said properties thus determining whether the protein will fold in the cytoplasmic environment of a microorganism to form a soluble biologically active or inactive protein or whether preferably high molecular weight protein aggregates will be formed. The folding equilibrium (formation of the soluble structured protein in relation to insoluble protein aggregates) can be influenced by the selection of the fermentation and expression conditions. For instance, by growing the prokaryotic cells at reduced cultivation temperatures and/or non-optimal induction conditions (limited inductor concentration) the recombinant plasmid-encoded protein biosynthesis rate can be reduced, thereby preventing or reducing an accumulation of the protein to form insoluble protein aggregates (cf., e.g., Kopetzki, E., et al., Mol. Gen. Genet. 216 (1989) 149–155; and EP 0 300 425). In other instances, it is desired, however, to prepare the recombinant protein via the route of inclusion bodies. Accordingly, an objective of such methods is to obtain a high yield of recombinant protein in the inclusion bodies. In this connection, it should be kept in mind, however, that other parameters, too, are of high importance in recombinant gene expression in prokaryotes, such other parameters being, for example, to achieve a recombinant gene expression as high as possible and to prevent undesired post-translational modification.

SUMMARY OF THE INVENTION

The present invention is an improved method for increasing the yield of insoluble denatured desired recombinant polypeptide comprising the additional step of an incubation at an unphysiologically elevated temperature following fermentation.

DETAILED DESCRIPTION OF THE INVENTION

The object of the invention therefore is a method for the recombinant production of a desired polypeptide by expressing a nucleic acid encoding said polypeptide in a microbial host cell, preferably prokaryotic host cell, forming in the cytoplasm of said host cell inclusion bodies containing said polypeptide, isolating the inclusion bodies, solubilizing and naturing the polypeptide, said method being characterized in that after fermentation the host cell or the host cell content is incubated at a temperature of 40° C. or higher, preferably 45° C. or higher, for at least 10 minutes, preferably for 10 to 180 minutes, and subsequent isolation of insoluble polypeptide from the host cell.

The method according to the invention is performed in aqueous media and usually carried out at temperatures between 40 and 60° C., preferably at 45° C. Higher temperatures contribute only very little to the effect according to the invention and may result in irreversible denaturation of the polypeptide.

Insoluble inclusion bodies are formed during recombinant expression of polypeptides in microbial host cells. Inclusion bodies are refractile aggregates of protease-resistant misfolded desired protein that occur upon over-expression of the encoding gene (Misawa, S., and Kumagai, I., Biopolymers 51 (1999) 297–307).

Surprisingly, by the incubation of the host cells containing the desired recombinant polypeptide at such unphysiologically elevated temperatures the desired polypeptide accumulates as insoluble inclusion bodies. Therefore, the yield of desired polypeptide in the insoluble portion of the fermentation batch can be enhanced. The duration of incubation and the incubation temperature are uncritical per se. With increasing incubation time and at higher incubation temperatures, at first a larger amount of inclusion bodies is formed. A very long duration of incubation and very high incubation temperatures, however, result in the polypeptide being changed irreversibly, for instance, by irreversible denaturation by heat. The person skilled in the art can now easily find out the optimum conditions for the recombinant production of the polypeptide of interest by carrying out simple experiments. In such experiments, it has been found that a considerable increase in the yield of recombinant polypeptide—containing inclusion bodies can be achieved, for instance, by post-incubation at 45° C. for one hour.

Suitable prokaryotic host cells for recombinant gene expression are, for example, gram-negative or gram-positive organisms, such as, e.g., *E. coli* and *Bacillus subtilis*. Suitable *E. coli* strains are, for instance, *E. coli* K12 strains such as UT5600, HB101, XL1, X1776 and W3110. However, other enterobacteriaceae as well as microorganisms such as *Klebsiella*, *Salmonella* or *Bacillus subtilis*, *Pseudomonas* or *Streptomyces* are also suitable as host cells. Also suitable as host cells are yeast strains, such as, e.g., *Saccharomyces*, *Pichia*, *Hansenula*, *Kluyveromyces* and *Schizosaccharomyces*.

The nucleic acid coding for the polypeptide is usually inserted in an expression vector. Suitable vectors are well-known to one skilled in the art and are, for example, plasmids or phages.

The fermentation of the host cells is also accomplished according to methods known to one skilled in the art.

Usually, the cells are first incubated at the fermentation temperature or up to 37° C. After a predetermined number of cells has been reached (measured via the optical density of the fermentation broth/cell suspension), the expression of the recombinant polypeptide is induced and cultivation is performed until the stationary phase is reached (in the case of batch cultures). After completion of cell growth, the cells are harvested and the inclusion bodies are isolated and processed by solubilization and naturation according to known methods. The additional incubation step according to the invention is appropriately inserted in this procedure. This implies that, for example, after completion of fermentation, simply the temperature of the fermentation batch is increased and subsequently the cells are harvested. Likewise, the cells can, of course, also be harvested and incubated according to the invention in suspension before or after lysis. Therefore fermentation is complete if the cell suspension is harvested and removed from the fermenter, the cell growth is inhibited otherwise or if the temperature of the cell suspension is raised according to the invention to 40° C. and more which inhibits also the further growth of the host cell.

The fermentation temperature can be in the usual range for recombinant production of polypeptides in microbial host cells. The fermentation temperature is preferably 30° C. or lower, especially if an N-terminal processing (e.g., N-terminal cleavage of methionine of the desired polypeptide) is desired. Such an N-terminal processing is performed enzymatically by endogenous enzymes of the host cell during fermentation. Particularly preferably, the range of temperature is between 18 and 28° C., and most preferably, between 22 and 26° C.

The following examples, references, sequence listing and figure are provided to aid the understanding of the present invention, the true scope of which is set forth in the appended claims. It is understood that modifications can be made in the procedures set forth without departing from the spirit of the invention.

Starting Material

The E. coli host/vector system (E. coli host strain and basic vector) employed for the expression of the genes/polypeptides according to the invention is described in U.S. Pat. No. 6,291,245.

General Methods

Recombinant DNA Technique

Standard methods were used to manipulate DNA as described in Sambrook, J., et al., Molecular cloning: A laboratory manual; Cold Spring Harbor Laboratory Press, Cold Spring Harbor, N.Y., 1989. The molecular biological reagents were used according to the manufacturer's instructions.

Polypeptide Determination

The polypeptide concentration for the multimeric T-repeat fusion polypeptide and interferon-α-2a was estimated by determining the optical density (OD) at 280 nm, using the molar extinction coefficient calculated on the basis of the amino acid sequence [T-repeat: ε=148680 cm²/mol; IFN-α-2a: ε=18020 cm²/mol].

EXAMPLE 1

Synthesis of the T-Repeat Fusion Gene 1.1 Gene Design of the T-Repeat Fusion Gene The artificial T-repeat fusion gene encodes a fusion polypeptide of 217 amino acids having a molecular weight of 27,242 D. The fusion polypeptide is composed of the N-terminal 13 amino acids of human interferon-α-2a (MCDLPQTHSLGSR (SEQ ID NO:1); carrier peptide) and 5 copies of the inhibitory HIV peptide T-1357 (WQEWEQ-KITALLEQAQIQQEKNEYELQKLDKWASLWEWF (SEQ ID NO:2), target peptide), which are connected via trypsin-cleavable peptide linkers (GR).

In order to insert the T-repeat structural gene into the E. coli expression plasmid pBRori-URA3-LacI-RFN-Edel (production and description: see Example 2), a synthetic ribosomal RBSII binding site and a singular EcoR1 cleavage site were inserted upstream at the 5' end and a singular CelII restriction endonuclease cleavage site upstream at the 3' end.

1.2 Gene Synthesis of the T-Repeat Fusion Gene

The RBSII T-repeat gene which is about 690 bp long and flanked by a singular EcoRI and CelII restriction endonuclease cleavage site was prepared from oligonucleotides by chemical synthesis. The double-stranded RBSII T-repeat gene was assembled by annealing and ligation of the oligonucleotides and subsequently cloned as an EcoRI/CelII fragment of a length of 691 bp into an E. coli plasmid. The desired plasmid was designated pT-repeat. The predetermined DNA sequence of the cloned RBSII T-repeat gene was confirmed by DNA sequencing.

EXAMPLE 2

Construction of the E. coli Expression Plasmids 2.1 Construction of the Starting Plasmid pBRori-URA3-LacI-RFN-Edel The plasmid pBRori-URA3-LacI-RFN-Edel is a vector for the expression of interferon-α-2a (IFN-α-2a) in E. coli. It is based on the IFN-α-2b expression plasmid OripBR-URA3-EK-IFN (U.S. Pat. No. 6,291,245). pBRori-URA3-LacI-RFN-Edel differs from OripBR-URA3-EK-IFN by an additionally present lacI repressor gene and an IFN-α-2a gene instead of an IFN-α-2b gene. IFN-α-2a and IFN-α-2b differ only by one amino acid at position 21 (Lys21Arg exchange). The lacI repressor gene comes from plasmid pUHA1 (Stüber, D., et al., System for high-level production in Escherichia coli and rapid application to epitope mapping, preparation of antibodies, and structure-function analysis; In: Immunological Methods IV (1990) 121–152). It was amplified by polymerase chain reaction (PCR) according to the method described by Mullis, K. B., and Faloona, F. A., In: Methods Enzymol. 155 (1987) 335–350, using the primers N1 (SEQ ID NO:3) and N2 (SEQ ID NO:4)

```
              NotI
N1:   5'-AAAAAAGCGGCCGCGACAATTCGCGCGCGAAGGCG-3'

NotI
N2:   5'-AAAAAAGCGGCCGCTCACTGCCCGCTTTCCAGTCGG-3'
``` and subsequently ligated as a NotI fragment of a length of about 1210 bp into the singular NotI cleavage site of OripBR-URA3-EK-IFN.

2.2 Construction of the Expression Vector pBRori-URA3-LacI-T-Repeat

The T-repeat gene was isolated as an EcoRI/CelII fragment of a length of about 690 bp from the plasmid pT-repeat (see Example 1.2) and subsequently ligated into the ca. 3.1 kbp long pBRori-URA3-LacI-RFN vector fragment digested with EcoRI and CelII. The desired plasmid pBRori-URA3-LacI-T-repeat was identified by restriction mapping and the subcloned T-repeat gene was verified again by DNA sequencing.

EXAMPLE 3

3.1 Expression of the T-Repeat Gene in E. coli

For the expression of the fusion gene according to the invention there was employed an E. coli host/vector system which enables an antibiotic-free plasmid selection by complementation of an E. coli auxotrophy (PyrF) (U.S. Pat. No. 6,291,245).

3.2 Transformation and Cell Production by Complementation of a pyrF Auxotrophy in Selective Medium In order to produce cells useful for expressing the T-repeat gene, an E. coli K12 strain [designated UT5600 (ΔpyrF)] was transformed with the expression plasmid pBRori-URA3-LacI-T-repeat described in Example 2.2. The transformed UT5600(ΔpyrF)/pBRori-URA3-LacI-T-repeat cells were first grown on agar plates and subsequently in a shaking culture in M9 minimal medium containing 0.5% casamino acids (Difco) up to an optical density at 550 nm ($OD_{550}$) of 0.6–0.9 and subsequently induced with IPTG (1–5 mmol/l final concentration). After an induction phase of 4–16 hours at 22–37° C., the cells were harvested by centrifugation, washed with 50 mmol/l potassium phosphate buffer, pH 6.5, and stored at −20° C. until further processing.

EXAMPLE 4

Transformation and Cell Production for the Expression of IFN-α-2a

For expression of the IFN-α-2a gene there was used an E. coli host/vector system enabling an antibiotic-free plasmid selection by complementation of an E. coli auxotrophy (PyrF) (U.S. Pat. No. 6,291,245).

For the production of cells for expressing IFN-α-2a, E. coli K12 strain UT5600 (ΔpyrF) was transformed with the expression plasmid pBRori-URA3-LacI-RFN-Edel described in Example 2.1. The transformed UT5600 (ΔpyrF)/pBRori-URA3-LacI-RFN-Edel cells were first grown on agar plates and subsequently in a shaking culture in M9 minimal medium containing 0.5% casamino acids (Difco) at 22–37° C. up to an optical density at 550 nm ($OD_{550}$) of 0.6–0.9 and subsequently induced with IPTG (1–5 mmol/l final concentration). After an induction phase of 4–16 hours at 22–37° C., the cells were harvested by centrifugation and washed with 10 mmol/l potassium phosphate buffer, pH 6.8.

EXAMPLE 5

Expression Analysis

The portion of soluble and insoluble IFN-α-2a and T-repeat fusion polypeptide present after the completion of cell growth, fermentation and post-fermentation was analyzed in cell lysates by SDS polyacrylamide gel electrophoresis (PAGE), staining with Coomassie Brilliant Blue R dye and densitometric analysis. Separation of the cell lysates into a soluble (supernatant) and an insoluble fraction (IB's and insoluble cell components) was achieved by means of centrifugation.

For this purpose, cell pellets from 3 $OD_{550}$ units each (1 $OD_{550}$=1 ml cell suspension with an $OD_{550}$ of 1) of centrifuged culture medium were resuspended in 0.25 ml 10 mmol/l potassium phosphate buffer, pH 6.8, and the cells were lysed by ultrasonic treatment (2 pulses of 30 s at 50% intensity). The insoluble cell components were sedimented (14,000 rpm, 5 min) and the supernatant was admixed with 1/5 volumes (vol) 5×SDS sample buffer (1×SDS sample buffer: 50 mmol/l Tris-HCl, pH 6.8, 1% SDS, 50 mmol/l DTT, 10% glycerol, 0.001% bromophenol blue). The insoluble cell debris fraction (pellet) was resuspended in 0.3 ml 1×SDS sample buffer and the samples were incubated for 5 min at 95° C. and again centrifuged. Subsequently, the polypeptides were separated by SDS polyacrylamide gel electrophoresis (PAGE) (Laemmli, U. K., Nature 227 (1970) 680–685), stained with Coomassie Brilliant Blue R dye and subsequently the relevant gel bands were analyzed densitometrically.

EXAMPLE 6

6.1 10 l High Cell Density Fermentation of E. coli for the Recombinant Production of T-Repeat Preculture In order to prepare the preculture, 300 ml M9 plus medium (M9 medium supplemented with 0.5% casamino acids and 0.9 g/l Trp, Pro and Leu each) was inoculated with 1 ml of a glycerol stock of E. coli UT5600ΔpyrF/pBRori-lacI-T-repeat in a 1000 ml Erlenmeyer flask. The culture was incubated for about 6 hours at 37° C. on an excenter shaker with 150 rpm until an $OD_{578\,nm}$ of 3.0 was reached.

10 l Fed-Batch Main Fermentation

At the beginning of fermentation, the preculture was transferred into a 10 liter fermenter. The main culture was grown in defined M9 salt medium containing 1.4% glycerol instead of glucose, 2% casamino acids and 0.1% of the amino acids Trp, Leu and Pro each, at 25° C. up to an $OD_{578\,nm}$ of 20. Subsequently, feeding of the culture with a glycerol yeast dosage (stock solution: 30% yeast extract and 33% glycerol) was started, the flow rate of which was varied between 0.8 and 3.5 ml/min depending on the development of the pH value of the culture, thereby avoiding any further addition of correction aids ($H_3PO_4$, KOH). The pH was maintained at pH 7.0, the $pO_2$ value was held at 50% by controlling the rpm.

At an $OD_{578\,nm}$ of 70 1.5 mmol/l IPTG was added and the gene/polypeptide expression was induced. The fermentation was terminated at an $OD_{578nm}$ of 160–180.

6.2 10 l High Cell Density Fermentation of E. coli for the Recombinant Production of Interferon-α-2a Preculture In order to prepare the preculture, 500 ml M9 medium supplemented with 0.5% caseamino acids and 0.9 g/l Trp, Pro and Leu each was inoculated with about 1.5 ml of a glycerol stock of E. coli UT5600ΔpyrF/pBRori-URA3-lacI-RFN in a 2 l Erlenmeyer flask. The culture was incubated for about 10 hours at 37° C. and 130 rpm (shaker) until an $OD_{546\,nm}$>2 was reached.

Fermentation

For fermentation, a complex medium on a yeast-glycerol basis was employed. The culture was carried out at 25° C. and a pH value of 7.0. When an $OD_{456\,nm}$ of 10 was reached, a glycerol yeast dosage was started, which additionally contained the amino acid L-methionine. Induction with 0.5 mM IPTG took place at an $OD_{546\,nm}$ of 50. Then the fermentation temperature was increased from 25° C. to 45° C. for a period of two hours. As a result of the high temperature, the expression product which had so far been present almost entirely in soluble form was converted into inclusion bodies. Subsequently, the biomass was harvested and the polypeptide was isolated.

EXAMPLE 7

Incubation of the Cells after Fermentation

After completion of fermentation, the cells were incubated at 45° C. for 1 h in the fermenter, while stirring, before being harvested by centrifugation.

The cells were analyzed in regard to the expressed polypeptides (soluble portion versus insoluble portion) as described in Example 5.

| Polypeptide | Standard fermentation at 25° C. | | Incubation at 45° C./1 h | |
|---|---|---|---|---|
| | Supernatant (soluble) | Pellet (insoluble) | Supernatant (soluble) | Pellet (insoluble) |
| IFN-α-2a | >95% | <5% | <2% | >98% |
| T-repeat | 40% | 60% | <2% | >98% |

Analogous results were obtained under the post-incubation conditions 42° C./1.5 h, 50° C./1 h. or 50° C./45 min.

LIST OF REFERENCES

Clark, E. D., Curr. Opin. Biotechnol. 12 (2001) 202–207
EP 0 300 425
EP-A 0 368 342
Kopetzki, E., et al., Mol. Gen. Genet. 216 (1989) 149–155
Laemmli, U. K., Nature 227 (1970) 680–685
Lee, S. Y., Trends Biotechnol. 14 (1996) 98–105
Lilie, H., Current Opinion Biotechnol. 9 (1998) 497–501
Mattes, R., Semin. Thromb. Hemost. 27 (2001) 325–336
Misawa, S., and Kumagai, I., Biopolymers 51 (1999) 297–307
Mullis, K. B., and Faloona, F. A., Methods Enzymol. 155 (1987) 335–350
Panda, A. K., et al., J. Biotechnol. 75 (1999) 161–172
Sambrook, J., et al., Molecular cloning: A laboratory manual; Cold Spring Harbor Laboratory Press, Cold Spring Harbor, N.Y., 1989
Stüber, D., et al., System for high-level production in *Escherichia coli* and rapid application to epitope mapping, preparation of antibodies, and structure-function analysis; In: Immunological Methods IV (1990) 121–152
U.S. Pat. No. 6,291,245

The invention claimed is:

1. In an improved method for the recombinant production of a polypeptide by expressing a nucleic acid encoding said polypeptide in a microbial host cell, forming in the cytoplasm of said host cell inclusion bodies containing said polypeptide, and isolating, and solubilizing under reducing conditions to renature the polypeptide, wherein the improvement comprises fermenting the host cell at a temperature of 30° C. or lower and thereafter incubating the host cell or the host cell content at a temperature of 40° C. to 60° C. for at least 10 minutes and subsequently isolating insoluble polypeptide from the host cell.

2. The method according to claim 1, wherein the incubation is carried out for 10 to 180 minutes.

* * * * *